US007884252B1

(12) United States Patent
Kolomeyer et al.

(10) Patent No.: US 7,884,252 B1
(45) Date of Patent: Feb. 8, 2011

(54) PROCESS FOR MAKING TRANS-ISOCARVEOL

(75) Inventors: Gennadiy G. Kolomeyer, Jacksonville, FL (US); Douglas A. Ferone, Jacksonville, FL (US)

(73) Assignee: LyondellBasell Flavors & Fragrances, LLC, Houston, TX (US)

( * ) Notice: Subject to any disclaimer, the term of this patent is extended or adjusted under 35 U.S.C. 154(b) by 0 days.

(21) Appl. No.: 12/799,119

(22) Filed: Apr. 19, 2010

(51) Int. Cl.
*C07C 35/18* (2006.01)
(52) U.S. Cl. ...................................... 568/826; 568/827
(58) Field of Classification Search ................. 568/826, 568/827
See application file for complete search history.

(56) References Cited

U.S. PATENT DOCUMENTS

| | | | |
|---|---|---|---|
| 3,956,404 A | 5/1976 | Walling et al. | |
| 3,957,856 A | 5/1976 | Ansari et al. | |
| 3,993,604 A | 11/1976 | Thomas et al. | |
| 4,306,099 A | 12/1981 | Fetizon et al. | |
| 5,994,598 A | 11/1999 | Chastain et al. | |
| 6,835,686 B2 | 12/2004 | Kolomeyer et al. | |

OTHER PUBLICATIONS

U.S. Appl. No. 12/799,118, filed Apr. 19, 2010, Kolomeyer et al.
Bessiere, Y. et al., "Isomerization of Limonene Epoxides, Allylic Rearrangement of p-Metntha-1(7),8-dien-2-ols: Preparation of Perilla Alcohol," *Journal of Chemical Research* (S), 1977, 304-305.
Tius, M., et al., "A Convenient Synthesis of (R)-(+)-Perillaldehyde," *Synthetic Communications*, 18, (16&17), 1905-1911, (1988).

*Primary Examiner*—Sikarl A Witherspoon
(74) *Attorney, Agent, or Firm*—Jonathan L. Schuchardt

(57) ABSTRACT

A process for making trans-isocarveol, an intermediate useful in the manufacture of perillyl alcohol, is disclosed. The process comprises isomerizing a mixture comprising cis-limonene oxide (cis-LMO) and trans-limonene oxide (trans-LMO) in the presence of a phenolic modifier and a chromium catalyst. The process is performed at a temperature less than 220° C. to convert more than 50% of the cis-LMO to trans-isocarveol and less than 50% of the trans-LMO to cis-isocarveol. We surprisingly found that a mixture of cis- and trans-LMO can be selectively isomerized to produce mostly trans-isocarveol, which we discovered is the preferred isomer for making perillyl alcohol by direct isomerization.

10 Claims, No Drawings

PROCESS FOR MAKING TRANS-ISOCARVEOL

FIELD OF THE INVENTION

The invention relates to a process for making trans-isocarveol, an intermediate useful in the flavor and fragrance industry.

BACKGROUND OF THE INVENTION trans-Isocarveol is an intermediate useful for the production of perillyl alcohol, a naturally occurring terpene with antimicrobial and anticancer properties. Hydrogenation of perillyl alcohol provides 4-isopropyl cyclohexanemethanol, which is a valuable fragrance ingredient having a fresh, clean odor reminiscent of white petals and flower blossoms.

Synthetic approaches to perillyl alcohol have been reviewed (see U.S. Pat. Nos. 3,993,604 and 5,994,598) and fall into three groups. In a first approach, a terpene hydrocarbon (α-pinene, β-pinene, or limonene) is oxidized using an equimolar amount of a toxic or explosive reagent (benzoyl peroxide, lead tetraacetate, or selenium dioxide). U.S. Pat. No. 3,956,404, which uses benzoyl peroxide, is illustrative.

A second approach prepares perillyl alcohol by isomerizing oxide (see, e.g., U.S. Pat. Nos. 3,993,604; 4,306,099; and 5,994,598). These methods use an acidic catalyst, give low yields of the desired alcohol, and generate a large amount of wastewater. They often produce mixtures of isomers resulting from double bond migrations, and the by-products are difficult to remove. Some of the methods produce disubstituted derivatives that require an additional step to convert them to perillyl alcohol.

In yet another approach, 1,2-limonene monoxide (hereinafter "LMO" or "limonene oxide") is used as the starting material. A mixture of cis- and trans-LMO is isomerized to produce, respectively, trans-isocarveol and cis-isocarveol:

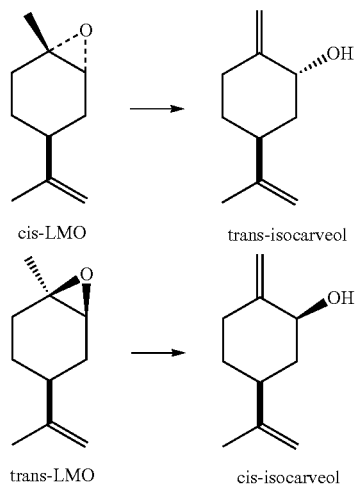

The isocarveols are converted into ester or other derivatives that are in turn isomerized to perillyl alcohol derivatives. Finally, the perillyl alcohol derivatives are hydrolyzed to produce perillyl alcohol. For examples of this approach, see U.S. Pat. Nos. 3,993,604 and 3,957,856; *Synth. Commun.* 18 (1988) 1905, and *J. Chem. Research* (S) (1977) 304. Interestingly, the latter reference indicates that the isocarveols cannot be isomerized directly to perillyl alcohol, which is consistent with our failure to find any reference teaching such a direct isomerization.

Although a mixture of cis- and trans-limonene oxide is readily available as a starting material, the need to derivatize isocarveols and subsequently remove the ester or other protecting group undermines the value of the third approach. Ideally, perillyl alcohol could be produced directly from the isocarveols in a commercially viable process.

Assuming that such a direct isomerization is even possible, which isocarveol isomer, cis- or trans-, is the better starting material? Distillation is impractical for separating cis- and trans-LMO, and commercially available limonene oxide contains 50-65% of cis-LMO and 35-50% of trans-LMO. If one isocarveol isomer is, in fact, better than the other for making perillyl alcohol, how can the preferred isomer be made selectively from a mixture of cis- and trans-LMO?

In U.S. Pat. No. 6,835,686, we described a method for isomerizing a mixture of cis- and trans-LMO to give isocarveols (compound 3). See, in particular, Example 45, which utilizes 1.7 wt. % of chromium octoate catalyst, 0.5 wt. % of a phenolic activator, and reflux at greater than 220° C. for 2.5 hours such that conversion of the combined mixture of LMO isomers exceeds 99.5% (see Table 2 of the '686 patent). No information is provided about the relative amounts of trans- and cis-isocarveols obtained; however, a high conversion of both cis- and trans-LMO to the isocarveols is evident from the overall quantitative conversion.

SUMMARY OF THE INVENTION

The invention is a process for making trans-isocarveol. The process comprises isomerizing a mixture comprising cis-limonene oxide (cis-LMO) and trans-limonene oxide (trans-LMO) in the presence of a phenolic modifier and from 1 to 1000 ppm, based on the combined amounts of cis- and trans-LMO, of a chromium catalyst at a temperature less than 220° C. The process is performed under conditions effective to convert more than 50% of the cis-LMO to trans-isocarveol and less than 50% of the trans-LMO to cis-isocarveol.

We surprisingly found that a mixture of cis- and trans-LMO can be selectively isomerized to produce mostly trans-isocarveol. Through additional work, we discovered that under the right conditions, isocarveols can be directly isomerized to perillyl alcohol. Moreover, we found that trans-isocarveol is actually the preferred isomer for making perillyl alcohol this way (see copending application Ser. No. 12/799,118, filed Apr. 19, 2010). Consequently, a way to make trans-isocarveol selectively from a mixture of LMO isomers, particularly the commercially available 65:35 mixture of cis- and trans-LMO, offers considerable value.

DETAILED DESCRIPTION OF THE INVENTION

The inventive process comprises selectively isomerizing a mixture comprising cis-limonene oxide (cis-LMO) and trans-limonene oxide (trans-LMO). Limonene oxide suitable for use in the process is a mixture of cis- and trans-isomers, which have the structures indicated above.

Suitable limonene oxide is obtained from any convenient source, e.g., from the epoxidation of limonene. Commercially available limonene oxide contains 50-65% of cis-LMO and 35-50% of trans-LMO, and this is suitable for use in the inventive process. Limonene oxide that has been purified by distillation and therefore contains a higher proportion of cis-LMO (e.g., 82-88%) can be used if desired. Generally, however, this source will be less available because separation of LMO isomers by distillation is difficult.

The process is performed in the presence of a chromium catalyst and a phenolic modifier. Suitable chromium catalysts are typically stoichiometric or non-stoichiometric combinations of carboxylic acids or their derivatives and chromium oxides. Examples include chromium acetate, chromium acetonylacetonate, chromium octoate, chromium 2-ethylhexanoate, chromium heptanoate, chromium naphthenate, chromium stearate, chromium decanoate, and the like. A preferred catalyst is chromium octoate, which typically contains 10-12% Cr and is available commercially from Shepherd Chemicals.

The amount of chromium catalyst used is from 1 to 1000 ppm, based on the combined amounts of cis- and trans-LMO. A more preferred range is from 20 to 800 ppm, most preferably from 100 to 700 ppm. The amount of catalyst actually used will depend on the reaction temperature, time, nature of the chromium catalyst and phenolic modifier, and other factors that are within the skilled person's discretion.

Suitable phenolic modifiers include phenol, alkyl-substituted phenols (e.g., cresols, isopropylphenols, tert-butylphenols, dimethylphenols, di-t-butylphenols, carvacrol, thymol), chlorophenols, hydroxyphenols, alkoxyphenols, nitrophenols, and the like, and mixtures thereof. Aminophenols, such as 2-aminophenol, are particularly preferred. For additional examples of suitable phenolic modifiers, see U.S. Pat. No. 6,835,686, the teachings of which are incorporated herein by reference.

The amount of phenolic modifier needed will also depend on numerous factors, as indicated above for the catalyst. Generally, however, the amount used will be within the range of 1 to 5000 ppm, based on the combined amounts of cis- and trans-LMO. A more preferred range is from 100 to 2000 ppm, most preferably from 500 to 1000 ppm.

The process is performed under conditions effective to convert more than 50% of the cis-LMO to trans-isocarveol and less than 50% of the trans-LMO to cis-isocarveol. We surprisingly found that under mild enough conditions, cis-LMO isomerizes to trans-isocarveol more rapidly than trans-LMO isomerizes to cis-isocarveol. Our earlier work (see, e.g., U.S. Pat. No. 6,835,686, Example 45) indicated no particular isomer preference in the LMO isomerization process using a chromium catalyst and phenolic modifier. However, by carefully controlling the isomerization conditions, we deduced that cis-LMO is actually the more reactive isomer. This is an important finding because we also discovered that under certain conditions, isocarveols can be directly isomerized to perillyl alcohol (see copending application Ser. No. 12/799,118, filed Apr. 19, 2010), and that although both isocarveol isomers give perillyl alcohol, trans-isocarveol is much easier to convert:

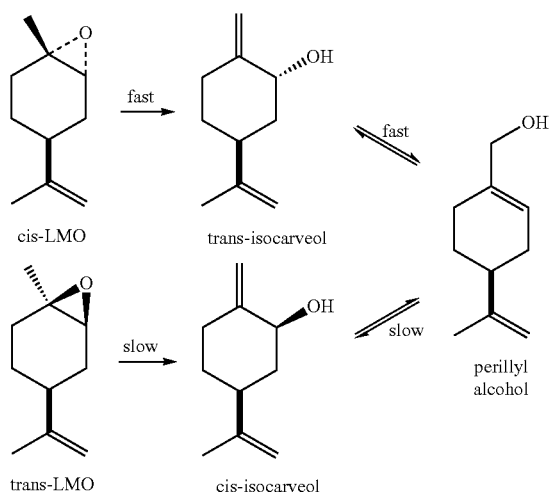

The isocarveol isomerizations are equilibrium controlled, but the trans isomer equilibrates to give the maximum amount of perillyl alcohol faster. Thus, trans-isocarveol is the more preferred starting material for making perillyl alcohol, and any method that favors its generation from LMO mixtures relative to the amount of cis-isocarveol produced is desirable.

Selective conversion of LMO mixtures to predominantly the trans-isocarveol isomer is preferably accomplished by controlling temperature, reaction time, catalyst choice and amount, modifier choice and amount, and other factors. The reaction temperature is kept below 220° C., preferably within the range of 150° C. to 219° C., more preferably from 200° C. to 218° C., and most preferably from 210° C. to 217° C. Reaction time is preferably minimized; the time needed to effect at least 50% conversion to trans-isocarveol at the preferred elevated temperatures will typically range from minutes to a few hours, preferably from 0.5 to 2 h, more preferably from 1 to 1.5 h.

Conversion is monitored by any convenient analytical method capable of determining the relative amounts of the LMO isomers, the isocarveol isomers, or both. Gas chromatography is particularly preferred.

Conditions are adjusted to convert more than 50% of the cis-LMO to trans-isocarveol and less than 50% of the trans-LMO to cis-isocarveol. More preferably, conversion of cis-LMO to trans-isocarveol is more than 75% and conversion of trans-LMO to cis-isocarveol is less than 25%. Most preferably, conversion of cis-LMO to trans-isocarveol is more than 85% and conversion of is trans-LMO to cis-isocarveol is less than 20%.

After the isomerization process has been performed to the desired degree of LMO isomer conversion, the reaction mixture typically contains cis-LMO (usually less than 15%), trans-LMO, trans-isocarveol (usually more than 50%), cis-isocarveol, and minor amounts of other impurities such as cis- and trans-carveol. The relative amounts of these components will depend on the proportion of cis- and trans-LMO isomers in the starting material, degree of conversion, and other considerations.

The trans-isocarveol is preferably isolated from the isomerization reaction mixture by distillation, which is usually performed at reduced pressure. The inventive process makes it possible to obtain highly pure trans-isocarveol from such a distillation. Normally, a mixture of LMO isomers that is enriched in trans-LMO is isolated as an initial cut, followed by the trans-isocarveol. The purity of the trans-isocarveol obtained from the distillation is preferably >95%, more preferably >98%, and most preferably >99%. The recovered LMO isomers can be used in other commercial processes, such as the process for making /-carvone (see, e.g., U.S. Pat. No. 6,835,686).

The asymmetric center of LMO (at C4 of the cyclohexyl ring) retains its configuration in the isomerization to trans-isocarveol. Thus, e.g., R-(+)-limonene oxide gives R-(+)-isocarveol, and the configuration is also retained upon subsequent direct isomerization to give R-(+)-perillyl alcohol.

The following examples merely illustrate the invention. Those skilled in the art will recognize many variations that are within the spirit of the invention and scope of the claims.

Example 1

Selective Preparation of Trans-Isocarveol

The procedure of U.S. Pat. No. 6,835,686 is generally followed, but with much less catalyst and less-stressed conditions. Thus, a mixture of limonene oxide (66% cis-, 34% trans-; 794 g), chromium octoate (12% Cr, product of Shepherd Chemicals, 0.53 g, 0.07 wt. %), and 2-aminophenol (0.66 g) is agitated and refluxed with a Dean-Stark trap for 1.5 h. The pot temperature at reflux increases from 198° C. to a maximum of 211° C. during the course of the reaction. After cooling, the reaction mixture is analyzed by gas chromatography (GC). It contains: cis-LMO, 3.6% (95% conversion); trans-LMO, 29.7% (13% conversion), and trans-isocarveol, 51.3% (82% selectivity based on reacted cis-LMO). Fractionation of this mixture on a distillation column (20 theoretical plates) at a reduced pressure affords a mixture of cis- and trans-LMO (240 g) and 99% pure trans-isocarveol (376 g). Additional trans-isocarveol can be recovered from recycle fractions.

Example 2

The procedure of Example 1 is repeated with limonene oxide (88% cis-, 12% trans-, 700 g), chromium octoate (0.4 g, 0.06 wt. %), and 2-aminophenol (0.48 g). The pot temperature at reflux increases from 198° C. to a maximum of 216° C. GC analysis of the product: cis-LMO, 12% (86% conversion); trans-LMO, 8% (20% conversion), trans-isocarveol, 70% (92% selectivity based on reacted cis-LMO), 3.4% trans-carveol, 0.1% cis-carveol, and 1.6% cis-isocarveol.

Example 3

The procedure of Example 2 is repeated except that the reaction mixture is allowed to reflux until the pot temperature reaches 217° C. GC analysis of the product: cis-LMO, 7.5% (92% conversion); trans-LMO, 7.9% (21% conversion), trans-isocarveol, 74.5% (91% selectivity based on reacted cis-LMO), 3.6% trans-carveol, 0.1% cis-carveol, and 1.8% cis-isocarveol. Fractionation of the reaction mixture at reduced pressure as described previously isolates the LMO isomer mixture for reuse and provides 99% pure trans-isocarveol.

Comparative Example 4

Non-Selective Preparation of Cis- and Trans-Isocarveols

The procedure of U.S. Pat. No. 6,835,686 is generally followed. Thus, a mixture of limonene oxide (65% cis-, 35% trans-), chromium octoate (1.7 wt. %), and 2-aminophenol (0.5 wt. %) are agitated and refluxed with a Dean-Stark trap as described in Example 1, above, except that the pot temperature is allowed to reach 224° C. and reflux continues for 2.5 h until conversion of both cis- and trans-LMO is essentially complete (99.5% total conversion). The product mixture contains trans-isocarveol (55%), cis-isocarveol (26%), cis- and trans-carveols (6%), and carvone (1%).

The trans-isocarveol product from Examples 1-3 is well-suited for further processing to produce perillyl alcohol and other chemicals. The mixture of cis- and trans-isocarveol produced from Comparative Example 4 is less desirable for making perillyl alcohol because cis-isocarveol undergoes direct allylic isomerization much more slowly compared with trans-isocarveol.

The preceding examples are meant only as illustrations. The following claims define the invention.

We claim:

1. A process for making trans-isocarveol, comprising isomerizing a mixture comprising cis-limonene oxide (cis-LMO) and trans-limonene oxide (trans-LMO) in the presence of a phenolic modifier and from 1 to 1000 ppm, based on the combined amounts of cis- and trans-LMO, of a chromium catalyst at a temperature less than 220° C. to convert more than 50% of the cis-LMO to trans-isocarveol and less than 50% of the trans-LMO to cis-isocarveol.

2. The process of claim 1 further comprising distilling trans-isocarveol from the isomerization reaction mixture.

3. The process of claim 2 wherein the distilled trans-isocarveol has a purity greater than 98%.

4. The process of claim 1 wherein the isomerization is performed at a temperature within the range of 150° C. to 219° C.

5. The process of claim 1 wherein the isomerization is performed at a temperature within the range of 200° C. to 218° C.

6. The process of claim 1 wherein the chromium catalyst is chromium octoate.

7. The process of claim 1 wherein the process is performed under conditions effective to convert more than 75% of the cis-LMO to trans-isocarveol and less than 25% of the trans-LMO to cis-isocarveol.

8. The process of claim 1 wherein the chromium catalyst is used in an amount within the range of 100 to 700 ppm.

9. The process of claim 1 wherein the phenolic modifier is 2-aminophenol.

10. The process of claim 1 wherein the phenolic modifier is used in an amount within the range of 100 to 2000 ppm based on the combined amounts of cis- and trans-LMO.

* * * * *